(12) United States Patent
Borzatta et al.

(10) Patent No.: US 9,044,012 B2
(45) Date of Patent: Jun. 2, 2015

(54) USE OF FORMULATIONS HAVING INSECTICIDAL ACTIVITY

(71) Applicants: Endura S. P. A., Bologna (IT); Sipcam S. P. A., Milan (IT)

(72) Inventors: Valerio Borzatta, Bologna (IT); Marco Bernardini, Lodi (IT); Carlotta Gobbi, Ravenna (IT); Giorgio Freschi, Piacenza (IT); Edoardo Russo, Piacenza (IT); Matteo Campanati, Bologna (IT); Francesca Borgo, Milan (IT)

(73) Assignees: ENDURA S.P.A., Bologna (IT); SIPCAM S.P.A., Milan (IT)

( * ) Notice: Subject to any disclaimer, the term of this patent is extended or adjusted under 35 U.S.C. 154(b) by 0 days.

(21) Appl. No.: 13/666,765

(22) Filed: Nov. 1, 2012

(65) Prior Publication Data

US 2013/0115261 A1 May 9, 2013

(30) Foreign Application Priority Data

Nov. 4, 2011 (EP) .................................... 11187834

(51) Int. Cl.
*A01N 25/28* (2006.01)
*A01N 53/00* (2006.01)
*A01N 43/40* (2006.01)

(52) U.S. Cl.
CPC ................ *A01N 25/28* (2013.01); *A01N 53/00* (2013.01)

(58) Field of Classification Search
USPC .................................. 424/408, 405; 514/341
See application file for complete search history.

(56) References Cited

U.S. PATENT DOCUMENTS

| 4,056,610 | A | * | 11/1977 | Barber et al. | ................. | 424/419 |
| 4,285,720 | A | * | 8/1981 | Scher | ............................ | 504/112 |
| 4,497,793 | A | | 2/1985 | Simkin | | |
| 6,077,522 | A | * | 6/2000 | Scher et al. | ................... | 424/408 |
| 2003/0119675 | A1 | | 6/2003 | Wolf et al. | | |
| 2004/0115280 | A1 | | 6/2004 | Podszum et al. | | |
| 2004/0120976 | A1 | | 6/2004 | Inui et al. | | |

FOREIGN PATENT DOCUMENTS

| EP | 0 183 999 A1 | 6/1986 |
| EP | 0 322 820 A1 | 7/1989 |
| EP | 0 747 116 A2 | 12/1996 |
| EP | 0 902 724 | 3/1999 |
| GB | 1 513 614 | 6/1978 |
| GB | 2 187 957 A | 9/1987 |
| WO | WO 97/14308 A1 | 4/1997 |
| WO | WO 03/051116 A1 | 6/2003 |
| WO | WO 2006/111839 A1 | 10/2006 |
| WO | WO 2009/000545 A2 | 12/2008 |
| WO | WO 2009/086914 A2 | 7/2009 |

OTHER PUBLICATIONS

E Y Sheu, "Microencapsulation of Lambda-Cyhalothrin for corp protection—the Zeon technology", 2000 BCPC Symposium Proceedings, pp. 57-64, No. 74.
Ian Shirley et al., "Delivery of biological performance via microencapsulation formaulation chemistry", Pest Management Science, 2001, pp. 129-132, vol. 57, 2001 Society of Chemical Industry.
P.J. Wege et al., :A Microencapsulated Formulation of Lambda-Cyhalothrin, Proceedings of the 3rd International Conference on Urban Pests, 1999, WM H. Robinson, F. Rettlich and G.W. Rambo.

* cited by examiner

*Primary Examiner* — Gina Justice
(74) *Attorney, Agent, or Firm* — Arent Fox LLP

(57) ABSTRACT

Use of formulations comprising polyurea microcapsules obtainable by interfacial polymerization of diphenylmethylen-4,4'-diisocyanate (MDI), optionally in admixture with polymethylenepolyphenylisocyanate (PAPI), said formulations having a prolonged knockdown and killing effect longer than at least 3 months, preferably at least of 6 months, still more preferably at least of 9 months from the application, wherein the microcapsules comprise:
an active principle selected from the pyrethroid and/or neo-nicotinoid classes,
synergizing agents selected between PEO and Verbutin,
the concentration of the active principle in the microcapsule as % by weight on the total of the microcapsule is comprised between 1 to and 60%
the average diameter of the microcapsules is comprised between 2 and 50 μm.

29 Claims, No Drawings

USE OF FORMULATIONS HAVING INSECTICIDAL ACTIVITY

The present invention relates to the use of formulations of microcapsules containing an active principle selected from the pyrethroid and/or neonicotinoid classes showing a very prolonged residual insecticidal activity even longer than three months, even longer than 6 months and even longer than 9 months from the application, and maintaining a high knockdown effect even shorter than one hour since the active principle has come into contact with the insect and having high insecticidal activity after 24 h and a high stability in time.

More specifically the present invention refers to the use of formulations of microcapsules having a very prolonged insecticidal activity suitable for professional, domestic applications, for environment disinfestation such as stables, sheds of domestic animals and residential and industrial areas.

Still more specifically the present invention relates to microcapsule formulations having a very prolonged insecticidal activity in particular for example against blattodea arthropods for example cockroaches, dipterons such as flies, hymenopters for example mosquitos, isopters for example ants, syphonopters for example fleas, acari for example spiders, coleopters for example cockchagers, isopters for example termites, dermopterans for example earwigs and rhyncotes for example bugs.

Various products to combat insects, in particular mosquitos are known in the art. Generally the used products can act in a preventive and curative way.

Among the products preventively acting there are, for example, compositions based on compounds such as ammonia and vegetable extracts. These products have a good efficacy but show some drawbacks such as for example the onset of skin inflammation and a limited duration in the time. Other products having a preventive action are the repellents which keep insects away, as for example the commercial product Autan®. These products or their compositions are directly applied on the skin with possible irritating effects and possible allergic reactions and, therefore, with trouble sensations.

Other products having a preventive efficacy are represented by the insecticide spirals that are cellulose derivative based compounds usually containing pyrethrum and/or pyrethroids. The disadvantage of these products resides in that the insecticide active principle is released in the environment and it can thus be inhaled.

Other products with preventive activity are represented by insecticide tablets or by heated LED emitters. These are apparatus containing insecticides that are optionally vaporized together with perfumes. The drawback of these products is the same as mentioned above of the inhalation.

Formulations containing microcapsules having the most various characteristics are known in the art, used in the above mentioned professional field. However microcapsules containing formulations having a prolonged activity in the time as indicated above preferably for longer than 6 months and 9 months, combined with a high stability and with reduced toxicity for use for example in the professional field are not known. For example the product Demand CS® or Icon CS® are active for three months, then they show a reduced activity.

Wege P. J. et al. in Proceeding of the Third International Conference on Urban Pests, WM H. Robinson, F. Rettlich and G. W. Rambo (Editors), 1999, describes microcapsules with polyurea wall containing lambda-cyhalothrin. The capsule wall is highly crosslinked, with a high ratio polymethylene-polyphenyl-isocyanate (PMPPI): toluene diisocyanate (TDI). This confers a relatively low permeability so that the active principle remains in the capsule. It is stated that the capsules remain intact for a long time on various surfaces allowing to control populations of insects such as flies, mosquitos, cockroaches and others by means of a sole application.

The data reported by Wege show that the insecticide activity is maintained up to 12 weeks. This article does not give any indication on a high knockdown and insecticidal effect after 6 months and 9 months from the application as knockdown and killing activity of the prepared capsules.

Shirley I. M. et al. in Pest Manag. Sci, 57,129-132 (2001) reports microcapsules with both slow and quick release of the active principle. As regards the active principle release in prolonged times the paper reports that these products are active up to three months.

Sheu E.Y. in 2000 BCPC Symposium Proceedings No. 74 discloses the Zeon technology of microencapsulation of lambda cyhalothrin that represents a quick release microencapsulation technique. It is based on the interfacial polymerization by using polymethylene-polyphenylisocyanate (PMPPI) acting as a monomer and toluene diisocyanate (TDI) as crosslinking agent.

The microcapsule sizes are comprised between 2 and 15 μm.

The so obtained product has a release rate of the active ingredient comparable to that of a concentrated emulsifier (EC) but a significantly lower toxicity for non-target organisms, besides an equivalent efficacy on the field.

Patent application WO 97/14,308 discloses compositions of microcapsules containing cypermethrin isomers (for example beta and theta cypermethrin) having a reduced toxicity but with good insecticidal activity.

The material of the capsule wall is made by one or more or the following components: cellulose derivatives, starch, gelatin, resins, polyamides, polyesters, polycarbonates, polyurethanes, polyureas. Inside the microcapsules together with the active principle also synergizing agents such as preferably PBO, sesame oil in the presence of other excipients can be present. The microcapsule sizes range from 1 to 2000 μm and can be obtained by coacervation or by interfacial polymerization. The release tests reported in the Tables of patent application WO 97/14,308 have been carried out with microcapsules obtained by coacervation. The Tables illustrate that surfaces treated with the following formulations:

a concentration of cypermethrin capsules having ethylcellulose walls and a diameter of 132 μm, a product in the form of "wettable powder" containing cypermethrin capsules having carbamide-urea-formaldeyde walls, with a diameter of 168 μm, maintain an effective insecticidal activity on domestic flies for the whole observation time of 25 weeks.

It has been found by the Applicants that the formulations prepared according to this patent application used in the Tables have not a high stability. This is a drawback since it is desirable to obtain microcapsules having a high prolonged activity in the time and having a high stability of the formulations in the time, for example of two years or longer.

In the description other polymers capable to form the microcapsule wall are mentioned. Among them, polyureas are mentioned in general, but no data are reported showing that the microcapsules obtained by interfacial polymerization can be used for pyrethroid slow release applications.

In particular no indication is given allowing to identify a specific class of polyureas allowing to obtain a prolonged insecticidal efficacy of the pyrethroid active principle after 3 months and showing after 6 and 9 months the same efficacy combined with a high stability of the formulation in time, for example of two years or longer.

U.S. Pat. No. 4,285,720 discloses a process for preparing capsules. The process is carried out by interfacial polymerization and comprises hydrolysis of a monomer isocyanate to form in situ an amine reacting with a monomer isocyanate to form thereafter the polyurea wall of the capsule. The process allows to obtain the microencapsulated material and allows to avoid the amine addition for obtaining the poly-urea. The process comprises the following steps:

preparation of an organic phase (i) comprising the material which must be encapsulated and a polyisocyanic monomer, preparation of the aqueous phase (ii) comprising water, a surfactant and a protective colloid, the dispersion being obtained by mixing (i) with (ii) at room temperature, heating of the dispersion by maintaining it at a temperature in the range of about 40° C. and 90° C. to obtain the polyurea microcapsule containing inside the encapsulated material.

The capsule average sizes range from 0.5 µm to 4,000 µm. The capsules prepared in the examples of this patent have sizes ranging from 1 to 30 µm. The capsules described in this document, as all the microcapsules of the prior art, have a prolonged effect with respect to the use of the indicated compositions (concentrated emulsions (EC) or wettable powders (WP)) which, on the contrary, have a short-term efficacy, generally of the order of some days.

The polyisocyanic monomers which can be used are aromatic polyisocyanates, aliphatic diisocyanates, high molecular weight linear diisocyanates and prepolymer isocyanates.

A list of monomer that can be used is reported, and it is stated that it is desirable and particularly preferable to use a combination of the above mentioned isocyanates to have good properties of controlled release of the active principle.

This patent does not report anything on the possible high residual activity even after 6 and 9 months from the application of the capsules both as knockdown effect and killing effect.

U.S. Pat. No. 4,497,793 discloses a process for preparing microencapsulated pyrethrins by interfacial polymerization. The first component forming the microcapsule is a polyisocyanate or an acyl chloride, which is mixed with the active principle with or without organic solvents. The mixture is emulsified in a continuous aqueous phase to which a polyfunctional amine is then added. The capsule wall is formed of polyamides or polyureas.

This patent does not say anything as to the fact that the capsules can have high insecticidal activity even after 3 months, preferably after 6 and 9 months from the application.

EP 747,116 describes a process for preparing microcapsules. The microcapsule polymers obtained by interfacial polymerization are polyureas, polyurethanes, polyamides, polycarbonates, polysulphonamides, polyureas being preferred.

Also in this patent nothing is said on the fact that the capsules can have efficacy even after 3 months, preferably after 6 and 9 months from the application.

DE 24 11 373 reports a method for controlling insects with a formulation containing pyrethrins or pyrethroids, preferably by adding synergizing agents.

Besides the insecticidal effect the method allows to obtain also a control of the repellent effect. Pyrethrins, pyrethroids and synergizing agents are used admixed or not, and are at least partially microencapsulated.

The microencapsulated active principles can be mixed with microcapsules containing synergizing agents, or are used with non encapsulated synergizing agents. Alternatively, the active principles and the synergizing agents are encapsulated together and then used. The capsules have sizes lower than 50 µm.

This patent does not report the types of polymers used for preparing the microcapsules. Furthermore no mention is made of the period of time, after the treatment, during which the release of the active ingredient results effective to inhibit the reappearance of the insects.

GB 1.513.614 discloses stable compositions in pyrethroid microcapsules. It is known that some pyrethroids are unstable in the presence of oxygen and of light. In the patent it is stated that the microencapsulation is not very useful to increase their stability since they very easily degrade also inside the microcapsules. The problem of the stability of pyrethroids inside the microcapsules is solved by preparing microcapsules having polyurea walls and comprising an UV absorber (photostabilizer). The microcapsules contain a liquid comprising a pyrethroid and a synergizing agent. The microcapsules have 1-100 µm sizes, preferably from 1 to 30 µm. In the examples the microcapsule walls are obtained by reacting polymethylene-polyphenylenisocyanate with a polyamine(tetraethylene pentamine). In the examples the insecticidal efficacy of these compositions has been monitored up to 60 hours from the application.

In this patent no indication is given on any high residual activity even after 3 months, preferably after 6 and 9 months from the application both as knockdown and killing activity of the capsules containing pyrethroids and/or neonicotinoids.

EP 183,999 relates to microcapsules containing pyrethroids and thereof preparation process. The process is carried out by interfacial condensation and the polycondensates are selected from the group comprising polyamides, polyamide-polyureas, polysulphonamides, polyesters, polycarbonates, polyurethanes and polyureas.

The process comprises the steps of:
preparation of an aqueous dispersion containing the pyrethroid in emulsion together with the first polymerization monomer under stirring, addition to the aqueous phase of the second monomer.

The first or the second monomer comprise at least partially a polyfunctional reactant containing at least two functional groups for the crosslinking. The functional groups are selected from amino, hydroxy, isocyanate, —COCl, —SO₂Cl. The microcapsules have a diameter from 3 to 130 µm, preferably from 10 to 45 µm. From the data reported in Table II it is observed that the microcapsules are active after more than 2 days (56 h) from the application.

However also this patent application does not concern microcapsules effective even after 3 months, preferably after 6 and 9 months from the application.

Patent application GB 2,187,957 relates to insecticidal/acaricidal compositions of microencapsulated pyrethroids in a capsule having a polymeric wall with an average diameter not greater than 80 µm, a wall thickness not larger than 0.3 µm and a ratio average diameter particle/thickness of the wall not lower than 250. The polymers forming the microcapsule wall are obtained by interfacial polymerization and are for example polyurethanes, poly-ureas, polyamides, polyamides-polyureas, polyesters, polycarbonates, polysuiphonates, polysulphonamides.

The Tables of the examples show that the microcapsules maintain a high insecticidal activity during the observation period of from 14 days to 28 days.

Also this patent application does not concern micro-capsules having a prolonged activity, that are effective even after 3 months, preferably after 6 and 9 months from the application.

EP 322,820 discloses microcapsules containing a pyrethroid insecticide having a 3-phenoxybenzyl group dissolved in the solvent 2-phenyl-xylyl-ethane. The microcapsule wall is formed by polyurethane and has a diameter not larger than 80 µm, a thickness not greater than 0.3 µm and a value of the ratio between average diameter of the microcapsule/thickness of the wall of 100-400. The formulation is particularly indicated for the insecticidal activity on cockroaches. Tables 3 and 4 of the examples show that the microcapsules maintain an insecticidal effect during the two months period of observation.

Also this patent application does not concern micro-capsules having a prolonged activity, that are effective also after 3 months, preferably after 6 and 9 months from the application.

EP 902,724 relates to a process for preparing insecticidal compositions in polyurea microcapsules allowing a relatively quick and complete release of the active principle after a short time. This patent discloses microcapsules having a quick release of the same order of concentrated emulsions.

US Patent application 2009/0130,156 relates to micro-capsule formulations allowing to improve the effectiveness of commercial active principles having an insecticidal, acaricidal, fungicidal or vermicidal activity by means of only one application, at the same time providing an effective treatment also for those species that have developed a resistance to the treatment with these agents. The active principle is released within some hours. The polymers of the microcapsule can be for example polyesters, polyamides, polyureas, polycarbamates, polyurethanes or urea/formaldehyde polymers.

US patent application 2003/0119,675 relates to micro-capsule suspensions wherein the microcapsule walls are obtained by reaction of mixtures of toluylene diisocyanate and 4,4'-methylenebis(cyclohexylisocyanate) with at least a diamine and/or a polyamine. The preferred amines are the aliphatic and alicyclic ones. The microcapsules contain an active ingredient which can be an insecticide selected from pyrethroids, neonicotinoids, triazole derivatives, phosphoric acid derivatives, or azolic fungicides, or triazolinone herbicides, benzonitriles or phenyluracyls. The microcapsules additionally contain a liquid aliphatic hydrocarbon having a boiling point higher than 160° C., an oleo-soluble dispersing agent and optionally one or more pesticides liquid at room temperature. The liquid phase is an aqueous phase and optionally comprises additives and non encapsulated active principles. These suspensions show high stability and also after a prolonged storage do not show formation of sediments. This patent application does not report anything as to the maintenance of the insecticidal activity, even after prolonged times from the application, of at least 3 months, preferably 6 and 9 months, and of the knockdown effect of the insecticide.

US patent application 2004/0115,280 relates to micro-capsules containing solid substances. In this patent application it is stated that the presence of liquids can pollute the area treated during the application and it reduces the microcapsule stability. The microcapsules are prepared by bringing a suspension of at least one active ingredient into contact with at least one polyisocyanate dispersed in water that reacts with a polyol or polyamine component. The active ingredient can be a fungicide, bactericide, insecticide, acaricide, vermicide, molluscicide, herbicide. The microcapsules sizes are comprised between 1 and 200 µm. Also this patent application does not report anything as to the maintenance of the insecticidal activity, even after prolonged times from the application, of at least 3 months, preferably 6 and 9 months, and of the knockdown effect of the insecticide.

US patent application 2004/0120,976 relates to micro-capsules containing a pyrethrin and a wall formed by a polymer, for example polyurethane, polyurea, polyamide, polyester and polycarbonate. The microcapsules have an average diameter in the range 5-100 µm and a thickness from 0.03 to 1 µm.

Pyrethrin can be in solution in an inert organic solvent. Synergizing agents such as PBO can also be added. The examples of this patent application relate to pyrethrin microcapsules having polyurethane walls. These microcapsules show an insecticidal activity also after 5 months from the application. This patent application does not report the insecticidal activity of these formulations after 6 or 9 months from the application.

WO 03/051,116 relates to the disinfesting treatment of parasites of domestic animals. In this patent application it is stated that a problem of the formulations for disinfesting the parasites of domestic animals is that the insecticide can be used at a dose that is toxic for the animal. Although many insecticides with a high effectiveness are known such as deltamethrin, their use for disinfesting domestic animals has been limited since these insecticides have a very high oral and topical toxicity.

This patent application discloses formulations containing microcapsules of insecticides having the characteristic of a low solubility in organic solvents and furthermore of being solid at room temperature. In this way the microcapsules release a constant but reduced dose of insecticide which is not toxic for the animal. The microcapsules containing the insecticide are prepared by interfacial polymerization oil in water. Preferably the microcapsule walls are of polyurea and have a diameter from 0.1 to 100 µm, preferably from 0.2 to 5 µm. In the examples micro-capsules having a diameter around 1 µm are used. Tests on the insecticide effectiveness for 24 hours are reported. In this patent application no indication is given on the insecticidal and knockdown activity prolonged in the time after 3 months, 6 months and 9 months from the application.

The need was therefore felt to have available micro-capsule formulations containing active principles selected from the classes of pyrethroids and/or neonicotinoids having a prolonged insecticidal activity at least longer than 3 months preferably of at least longer 6 months, more preferably of at least than 9 months from the application and maintaining a high knockdown effect even shorter than one hour since the active principle has come into contact with the insect and showing a high stability in the time of at least two years, as determined by the CIPAC test reported hereinafter.

It has been unexpectedly and surprisingly found by the Applicants that the use of microcapsule formulations containing an active principle selected from the pyrethroid and/or neonicotinoid classes solves the above mentioned technical problem. In said formulations the active principle shows a high insecticidal activity at least longer than 3 months, preferably of at least 6 months and 9 months according to the test reported hereinafter and a high knockdown effect after one hour from the application.

An object of the present invention is the use of formulations of microcapsules with polyurea walls, obtainable by interfacial polymerization of diphenylmethylen-4,4'-diisocyanate (MIDI), optionally in admixture with polymethylenepolyphenylisocyanate (PAPI), the microcapsules containing an active principle selected from the pyrethroid and/or neonicotinoid classes, the formulations showing a prolonged knockdown and insecticidal activity even longer than 3 months, even longer than 6 months and even longer than 9 months from the application, the average diameter of the capsules ranging from 2 to 50 µm, preferably from 3 to 30 µm, more preferably from 6 to 20 µm; the active principle concentration in the formulation expressed as percent by weight on the total of the microcapsule is comprised from 1% up to 60%, preferably from 2.5% to 55%, more preferably from 5% to 50%; synergizing agents selected from piperonyl butoxide (PBO) and 4-[1-(2-butin-1-yloxy)ethyl]-1,2-dimethoxy benzene (Verbutin) being present inside the microcapsule.

Preferably the polyurea of the microcapsule walls is obtainable by interfacial polymerization of diphenyl methylen-4,4'-diisocyanate (MDI) in the presence of polymethylenepolyphenylisocyanate (RAPT).

Polymethylenepolyphenylisocyanate is generally known, besides as PAPI, also as PMPPI or PMPI or PMDI or polymethylenepolyphenylpolyisocyanate or polymethylenephenylisocyanate [9016-87-9].

Preferably polymethylenepolyphenylisocyanate (PAPI) has a NCO functionality ranging from 2.3 to 3.

The polymethylenepolyphenylisocyanate molecular weight is generally in the range 300-400 dalton.

In the preferred compositions of the invention the weight amount of MDI with respect to PAPI (MDI:PAPI) is comprised between 100:0 to 20:80, preferably between 35:65 and 65:35.

The addition of synergizing agents is such that in the microcapsules there is a weight ratio synergizing agent/active principle comprised between 0.02 and 50, preferably 0.05-20, more preferably 3-10.

Preferably the synergizing agent is PBO.

Optionally solvents having a low environmental impact, i.e. solvents that are non toxic for the environment (the so called green solvents) are present inside the microcapsule.

The formulations of the microencapsulated active principle show advantages for the operator safety.

Optionally also TDI can be used as a further monomer in combination with MDI in the interfacial polymerization to obtain microcapsules with polyurea walls. Preferably TDI is used in combination with MDI and PAPI. The amounts by weight between MDI and TDI (MDI:TDI) range from 10:90 to 100:0, preferably from 30:70 to 100:0.

Preferably the green solvents of the present invention are selected from those having the following properties: low volatility, as defined according to ASTM D3539 or according to DIN 53170,
capability to solubilize the active principle at the temperature of 20° C., at least at a concentration of 1% by weight, preferably 5%, more preferably 10%, still more preferably at least 20% by weight,
substantial immiscibility with water, preferably total immiscibility with water.

Examples of solvents that can be mentioned are the following:
- $C_9$-$C_{20}$, preferably $C_{10}$-$C_{16}$ alkylbenzenes and their mixtures, wherein the alkyl can be linear or branched. Solvesso® 150, Solvesso® 200, Solvesso® 150 ND, Solvesso® 200 ND, preferably free from naphthalene residues, such as Solvesso® 150 ND and Solvesso® 200 ND, can for example be mentioned;
- $C_1$-$C_4$ alkyl esters of $C_3$-$C_{14}$ aliphatic bicarboxylic acids, as for example dimethyl glutarate, dimethyl succinate, dimethyl adipate, dimethyl sebacate, diisopropyl myristate or their mixtures, preferably DBE (mixture containing 55-65% weight/weight of dimethyl glutarate, 15-25% weight/weight of dimethyl succinate and 10-25% weight/weight of dimethyl adipate);
- $C_3$-$C_{10}$ alkyl esters of aliphatic $C_3$-$C_{10}$ carboxylic acids and aliphatic $C_3$-$C_{13}$ hydroxyacids, as for example Purasolv® EHL (ethylhexyl lactate);
- methyl esters of saturated or unsaturated $C_{12}$-$C_{22}$ fatty acids or their mixtures, preferably oleic acid and linoleic acid or their mixtures, for example biodiesel;
- $C_7$-$C_9$ alkyl esters of the acetic acid, for example heptylacetate (Exxate® 700, Exxate® 900).

Examples of pyrethroids that can be mentioned are Allethrin and d-Allethrin, Bifenthrin, Bioallethrin, Bioresmethrin, Cyfluthrin, β-Cyfluthrin, Cyhalothrin, γ-Cyhalothrin, λ-Cyhalothrin, Cypermethrin, α-Cypermethrin, β-Cypermethrin, θ-Cypermethrin, ζ-Cypermethrin, Cyclothrin, Deltamethrin, Esbiothrin, Esfenvalerate, Etofenprox, Phenothrin, d-Phenotrin, Fenproprathrin, Fenvalerate, Imiprothrin, Metofluthrin, Permethrin, Prallethrin, Resmethrin, Silafluofen, Tau-fluvalinate, Tetramethrin, d-Tetramethrin, Transfluthrin, pyrethrum extracts and their mixtures.

Furthermore pyrethroids can be both phototable and photolabile.

Among photostable pyrethroids the following can be mentioned: Bifenthrin, Cyfluthrin, β-Cyfluthrin, Cyhalothrin, γ-Cyhalothrin λ-Cyhalothrin, Cypermethrin, α-Cypermethrin, β-Cypermethrin, θ-Cypermethrin, ζ-Cypermethrin, Deltamethrin, Esfenvalerate, Etofenprox, Fenvalerate, Permethrin, Silafluofen, Transfluthrin, Tau-fluvalinate.

Among the photolabile ones the following can be mentioned: Allethrin and d-Allethrin, Bioallethrin, Bioresmethrin, Esbiothrin, Phenothrin, d-Phenothrin, Fenproprathrin, Imiprothrin, Metofluthrin, Prallethrin, Resmethrin, Tetramethrin, d-Tetramethrin, pyrethrum extracts and their misture.

Pyrethroids, as already mentioned, can also be in. a non esterified form, as for example Etofenprox and Silafluofen.

Examples of neonicotinoids are Acetamiprid, Chlothianidin, Imidacloprid, Thiacloprid, Thiamethoxam and AKD1022.

The formulations of the invention were found stable at least for two years when subjected to the stability test according to CIPAC MT 46.

As said, the formulations of the invention containing pyrethroids and/or neonicotinoids and having a very prolonged insecticidal activity and a prolonged knockdown effect are particularly suitable for professional applications, for domestic applications, for environment disinfestations as stables, sheds of domestic animals and residential and industrial areas.

The formulations of the invention are particularly suitable against blattodea arthropods, for example cockroaches, dipterons such as flies, hymenopters for example mosquitos, isopters for example ants, syphonopters for example fleas, acari for example spiders, coleopters for example cockchafers, isopters for example termites, dermopterans for example earwigs and rhyncotes for example bugs.

The test for determining the killing effectiveness prolonged in time and the knockdown effect of the formulations of the invention has been carried out by evaluating the biological activity of the formulations on susceptible insect offspring bred in colonies maintained according to standard breeding procedures by using 2-3 days old flies (Musca domestica) and 2-3 days old mosquitos (*Culex* spp.) of both sexes, and fully-grown mixed sex cockroaches (*Blattella germanica*);
the solutions for the treatment of insects have been prepared by dilution in water at the desired application dose, then applied on unglazed and/or glazed tiles (diameter 10 cm) by means of Potter Precision Laboratory Spray Tower Automatic Model (Burkard Scientific); the Potter Tower has been previously calibrated to obtain an output spray of 40 ml±10% per m² by operating on pressure, application rate, nozzle type;

after application of the formulation, the tiles have been maintained under controlled conditions in an air-conditioned room at 25° C. in the presence of relative humidity 50-70% and light/dark photoperiod equal to 16/8 hours wherein the light source is a neon lamp;

in the test the insects have been maintained in contact with the surface treated for one hour and then the knockdown percentage was evaluated; the insects have been then transferred in a container not treated and fed with a sugar water solution; after 24 hours the percent mortality (killing effect) was evaluated; the test has been repeated at different times after one, three, six and nine months, making three replicates for each experiment.

More specifically in tests on mosquitos 10 mixed sex individuals have been introduced into a plastic cone assembled on the unglazed or glazed tile according to the WHO protocol (1990) "Instructions for the Bio-assay of insecticidal deposits on wall surfaces";

in the tests on flies, 10 individuals of both sexes have been introduced into an aluminum cage (10 cm diameter, 3 cm height) assembled on the unglazed or glazed tile;

in the tests on cockroaches, 5 individuals of both sexes have been introduced into an aluminum cage (10 cm diameter, 3 cm height) assembled on the unglazed or glazed tile.

In parallel tests an untreated control was run for establishing the natural mortality of the insects used in the tests. The test has been repeated at various times, after one, three, six and nine months, by making three replicates for each experiment.

Preferably the solutions for the insect treatment are applied on tiles in particular according to the method described in "Laboratory apparatus for applying direct sprays and residual films", The Annual of Applied Biology, vol. 39, No. 1, Mar. 1, 1952.

It is a further object of the present invention formulations of microcapsules with polyurea walls obtainable by interfacial polymerization of isocyanic monomers formed of diphenylmethylen-4,4'-diisocyanate (MDI), optionally polymethylenepolyphenylenisocyanate (PAPI), and still more optionally in the presence of tolylendiisocyanate (TDI), comprising an active principle selected from the pyrethroid and/or neonicotinoid classes, having a prolonged insecticidal activity of the active principle of at least three months, preferably of at least 6 months, still more preferably of at least 9 months from the application according to the above mentioned test and maintaining a high knockdown effect even shorter than one hour according to the above test, and also high stability in the time, the concentration of the active principle expressed as percent by weight on the total of the microcapsule being in the range from 1% up to 60%, preferably from 2.5% to 55%, more preferably from 5% to 50%, the average capsule diameter being comprised between 2 and 50 μm, preferably from 3 to 30 μm, more preferably from 6 to 20 μm and the microcapsules containing synergizing agents selected from piperonylbutoxide (PBO) and Verbutin.
Preferably the Synergizing Agent is PBO.

Preferably the polyurea microcapsules are obtainable by interfacial polymerization of diphenylmethylen-4,4'-diisocyanate (MDI) in the presence of polymethylenepolyphenylisocyanate (PAPI), The polymethylenepolyphenylenisocyanate is as defined above. Optionally TDI can also be used as a further monomer in combination with MDI, Preferably TDI is used in combination with MDI and PAPI.

The weight ratio synergizing agent/active principle, the amount by weight of MDI with respect to PAPI and the ratio by weight of MDI with respect to TDI are as defined above.

Optionally the microcapsules also contain the above reported green solvents, that as known have a low environmental impact.

The microcapsule formulations of the present invention can contain other optional components such as dispersants, thickeners, antifoam, antifreeze, antimould agents, photoprotectors and adhesive agents, etc.

Among dispersants, the following can be mentioned: ligninsulphonates, for example sodium ligninsulphonates, for example Reax® 100M, Reax® 88 B, Kraftsperse® 25 M and Ultrazine® NA, and calcium ligninsulphonates, for example Borrement® CA, block polymers containing ethylenoxide and/or propylenoxide blocks, for example Pluronic®PE 6400, Pluronic® 10400, polycarboxylates, for example sodium polycarboxylates, as Geropon® TA 72.

Among thickeners xanthan rubber (Rhodopol®) can be mentioned; among antifoam agents, silicone compounds, as for example Defomex® 1510, can be cited.

Among antifreeze compounds, inorganic salts, as calcium nitrate, sodium carbonate, calcium chloride, sodium chloride, glycols such as monopropylene glycol, dipropylene glycol, monoethylene glycol, glycerine, can be mentioned.

As antimould agents, substituted triazines, as for example Amebact® C, and benzoisothiazolinones, as Proxel® GXL, can for example be mentioned.

Among adhesivants, polyvinyl pyrrolidone such as PVP®K30, PVP®K15, PVP®K90, vinylpyrrolidone/vinylacetate copolymers as PVPVA, sugar as glucose, saccharose, can be mentioned.

Among photoprotectors, benzotriazoles, benzophenones and sterically hindered amines (HALS) can be mentioned.

Among benzotriazoles, the compounds are preferably selected from: 2-(2'-hydroxy-5-t-octylphenyl)benzotriazole and 2-(2'-ydroxy-3',5'-di-t-butylphenyl)-5-chloro-benzotriazole.

Among benzophenones, the compounds are preferably selected from: 2-hydroxy-4-methoxy benzophenone, 2-hydroxy-4-octyloxy benzophenone, 2,2'-dihydroxy-4,4'-dimethoxy benzophenone.

Among the sterically hindered amines, the compounds are preferably selected from: di(2,2,6,6-tetramethyl-4-piperinidyl)sebacate; di(1,2,2,6,6-pentamethyl-4-piperidinyl)sebacate; alpha-[[6-[[4,6-bis(dibutylamino)-1,3,5triazin-2-yl](2,2,6,6-tetramethyl-4-piperidinyl)amino]hexyl](2,2,6,6-tetramethyl-4-piperidinyl)amino]-omega-[4,6-bis(dibutylamino)-1,3,5-triazin-2-yl]-poly[[6-[butyl(2,2,6,6-tetramethyl-4-piperidinyl)-amino]-1,3,5-triazin-2,4-diyl][2,2,6,6 tetramethyl-4-piperidinyl)imino]-1,6-hexandiyl[2,2,6,6-tetramethyl-4-piperidinyl)imino]; the dimethylsuccinate polymer with 4-hydroxy-2,2,6,6-tetramethyl-1-piperidinethanol; the N,N' Polymer di(2,2,6,6-tetramethyl-4-piperinidyl)-1,6-hexan-diamine with 2,4,6 trichloro-1,3,5-triazine and 1,1,3,3-tetramethylbutylamine; polymethyl propyl-3-oxy(4((2,2,6,6-tetramethyl)piperidinyl siloxane; 1,3,5-triazine-2,4,6,-triamine, N,N'[1,2-ethandiyl di[[[4,6-bis[butyl(1,2,2,6,6-pentamethyl-4-piperidinyl)amino]-1,3,5-triazine 2-yl]-imino]-3,1-propandiyl]]-di[N',N"-dibutyl-N',N"-bis-(1,2,2,6,6-pentamethyl-4-piperidinyl)] or the following mixture: mixture of the polymer of dimethylsuccinate with 4-hydroxy-2,2,6,6-tetramethyl-1-piperidin ethanol and the polymer of N,N' di(2,2,6,6-tetramethyl-4-piperinidyl)-1,6-hexanediamine with 2,4,6 trichloro-1,3,5-triazine and 1,1,3,3-tetramethyl butylamine.

Benzotriazoles and sterically hindered amines are particularly preferred, Tinuvin®292 [41556-26-7] and Tinuvin® 326 [3896-11-5] are still more preferred.

As said, the microcapsule formulations of the present invention have a very prolonged insecticidal activity in time even up to 9 months, combined with a knockdown effect within one hour since the active principle has come into contact with the insect and at the same time they show a high stability.

As said, the formulations of the present invention show a prolonged knockdown and insecticidal activity even longer than 3 months, even longer than 6 months and even longer than 9 months from the application.

The formulations of the invention can be applied on manufactured articles, soils, industrial areas, etc. according the most suitable application method. The active principle is applied at the dose on the label.

As said, the microcapsule formulations of the present invention show a prolonged insecticidal activity, longer than 3 months, preferably of at least 6 months, still more preferably of at least 9 months from the application and maintain a high knockdown effect, even shorter than one hour since the active principle comes into contact with the insect and furthermore they show a high stability in the time (shelf life) of at least two years, as determined with the CIPAC test reported hereinunder.

It is a further object of the invention a process for preparing the microcapsules of the formulations of the invention comprising the following steps:
(1) preparation of an aqueous phase containing at least a surfactant;
(2) preparation of an oil phase containing an active principle selected from the pyrethroid and neonicotinoid classes, a synergizing agent selected from PBO and Verbutin and the isocyanic monomeric reactant methylenphenyien-4,4'-diisocyanate (MDI) optionally in the presence of polymethylenepolyphenylisocyanate (PAPI) that are used to form the polyurea of the microcapsule wall;
under stirring the oil phase (2) is added to the continuous aqueous phase (1) to obtain microcapsules with polyurea walls.

Optionally in step (2) green solvents can be added, if the active principle needs to be solubilized.

Preferably the obtained dispersion is left for a period of time from 2 to 8 hours at a temperature from 30° to 80° C. (maturation step).

The addition of the oil phase (2) to the aqueous phase (1) is preferably carried out under stirring such as to generate in the reactor a turbulent flow. It is thus obtained a dispersion/emulsion in a very short time, of the order from 0 to 20 minutes, preferably from 1 to 15 minutes.

Preferably in step (2) MDI is used in combination with polymethylenpolyphenylenpolyisocyanate (PAPI). PAPI is as defined above.

Optionally in phase (2) TDI in combination with MDI can be used as a further monomer. Preferably TDI is used in admixture in combination with MDI and PAPI.

The preferred synergizing agent is PBO.

The weight ratio synergizing agent/active principle, the amount by weight of MDI with respect to PAPI and the ratio by weight of MDI with respect to TDI are as defined above.

In the maturation step the maximum operating temperature depends on the stability of the encapsulated active principle.

Preferably the process of the invention is performed under conditions such as the active principle is in the liquid state during the preparation of the microcapsule.

If desired in the aqueous phase (1) as optional component a small amount from 0.1 to 30% by weight of an electrolyte, for example a salt, preferably inorganic, having a high solubility in water can be added. Generally salts that can be used are those of the first and second group of the periodic system. Examples of these salts are NaCl, $Ca(NO_3)_2$ etc.

In the oil phase (2) photoprotectors such as, for example, Tinuvin®292 e Tinuvin®326 can be added.

To complete the formulation the above reported optional components can be added.

The data obtained in the present invention show that the results are unexpected and surprising. In fact the Applicants were capable to obtain a formulation showing a knockdown and insecticidal activity at 3 months, being the knockdown and insecticidal activity even at 6 months and even at 9 months. Said activities are always higher than those of the corresponding formulations wherein the microcapsule polyurea walls were obtained by adding an amine in polymerization. That appears to be surprising and unexpected; in fact by preparing the microcapsule polyurea walls without adding any polyamine (the so called in situ polymerization), but by using MDI-di-isocyanate, optionally in the presence of polyisocyanates and/or di-isocyanates, it was possible to obtain a formulation with a prolonged and high knockdown and insecticidal activity, better than that shown by a corresponding formulation wherein the microcapsule polyurea wall was obtained by adding an amine in polymerization. See for instance the comparison between example 4 of the invention (in situ polymerization) vs. example 1 comparative wherein the polyurea has been obtained by adding an amine.

The present examples are given for illustrative purposes and are not intended to limit the scope of the present invention

EXAMPLES

Physico-Chemical Characterization

Inertia of the Green Solvent with Respect to the Capsule Walls

The inertia with respect to the capsule walls is evaluated according to the following test.

The solvent is left into contact with the encapsulated active principle for 48 hours at room temperature (20° C.)

Neither breaks of the capsule or significant swellings of the capsule must take place.

Stability of the Formulations on Dilution

The stability on dilution is evaluated by measurements of suspensibility (sedimentation) by using the official method CIPAC MT 161. The greater the suspensibility (lower sedimentation), the higher the formulation stability.

Accelerated Stability Test of the Formulations

This test is used to estimate the stability of the suspensions at room temperature for times longer than 1 year. The conditioning of the sample for 14 days at 54° C. corresponds to at least two years at room temperature.

According to the standard test CIPAC MT 46, at the beginning and after conditioning the formulation for 14 days at 54° C. (aging test), the following parameters: titre and encapsulation efficiency are determined on the formulation.

The active principle titre is determined by gaschromatography or by HPLC, depending on the physical characteristics of the compound. Methods for the quantitative analysis of pyrethroids and neonicotinoids using the above mentioned techniques are known in literature.

The encapsulation efficiency is determined by maintaining the formulation of the microcapsules (5 g) diluted up to the volume of 100 cc with n-hexane for 1 minute at room temperature (20° C.) under mild stirring. At the end the organic phase is recovered and the amount of insecticide present therein, which corresponds to the amount of the non encapsulated insecticide, is determined.

The ratio between:

(total insecticide amount−non encapsulated amount)/
Total insecticide amount wherein the total insecticide amount is that present in the whole formulation, gives the encapsulation efficiency.

Granulometry Test of the Microcapsules

The test is carried out by using a laser beam granulometer (Malvern Mastersizer). For the analysis 30-50 mg of the sample under examination are weighed. The instrument provides the granulometric distribution curve, as a measurement of the average granulometry the value in abscissas corresponding to the maximum height of the peak is taken.

Laboratory Test for Determining the Prolonged Insecticidal Efficacy in Time of the Formulations on Mosquito *Culex pipiens pipens* L. (Diptera, Culicidae)

The test was carried out at room temperature, under controlled conditions for 3 months, 6 months and 9 months. The insects were two days old adult insects of both sexes.

For the tests a chamber formed by a transparent cone with a 10 cm diameter was used that was positioned on an unglazed tile (biscuit) that is a raw clay composition, or on a glazed tile. The space between the cone edges and the tile was filled with cotton wool and then with adhesive tape.

The formulations described in the examples (see later on) were prepared the same day of their application on the tiles and used within one hour. Deionized water was used to dilute the formulations at the desired concentration. The so prepared formulations were applied to the tiles by means of a spray equipment Potter Spray Tower Automatic Model-Burkard Scientific.

The equipment was calibrated with running water by adjusting the spray pressure (about 1 bar), the application rate and the type of nozzle to obtain an output of 40 ml±10% per $m^2$.

10 adult mosquitos (of both sexes) were collected by means of a sucker and introduced into the chamber by gentle blowing. The mosquitos were kept for one hour in the chamber. At the end the knocked down insects were counted (knockdown effect). All the mosquitos were then recovered and placed in a vessel without insecticide. The mosquitos were then fed with a water and sugar solution soaked in cotton. After 24 hours under these conditions the dead insects (insecticide killing effect) were counted. For each treatment and for each dose of the test three replicates were made. In parallel an untreated control was run to determine the natural mortality of the insects used in the test.

The dose of active principle used in the tests was of 10.00 $mg/m^2$.

The comparative product used was the commercial product DEMAND CS® containing Lambda Cyhalothrin at a concentration of 9.67% (w/w).

The tiles were treated with the formulations at a concentration of active principle equal to 10.00 $mg/m^2$. After evaporation of water from the applied formulation the first test to evaluate the insecticidal activity (t=0) was carried out. The tiles were then placed in an incubator and kept under the following conditions:
temperature 25° C.
relative humidity 50-70%
period of light/darkness: 16 hours of light and 8 hours of dark.

The prolonged efficacy of the residual insecticidal action was evaluated after one month, three months, six months and 9 months from the treatment and subsequent exposure of the tiles under the above reported conditions. For each time and each formulation three replicates were made. For each determination new tiles previously treated as described above were used. During the test a control was run to establish the natural mortality of the insects.

The average mortality in the treated group was compared to that of the control group by using the Abbott formula:

$M\% = ((Mt-Mc)/(100-Mc)) \times 100$ wherein:
M %=correct mortality (%)
Mc=average mortality in the control group
Mt=average mortality in the experimentation group.

The mortality data were analyzed for the significance by suitable statistical methods, i.e. Dunnett's test, Student's test, ANOVA-MANOVA.

The samples prepared in examples, a commercial preparation of an emulsifiable concentrate (EC) of Deltamethrin (DTM) and Deltamethrin/PBO, in the same concentrations and in the same weight ratios used in the microcapsules and the commercial product Demand CS® containing 9.67%(w/w) of active principle Lambda Cyhalothrin, were analyzed for the insecticidal activity and knockdown effect.

The results are reported in Table 5.

Example 1 Comparative

Preparation of the Formulation of Microcapsules called CS1

In a 1000 ml glass reactor an organic solvent solution is prepared formed of 31 g of Deltamethrin 99% purity, 158 g of piperonyl butoxide 94% purity and 200 g of Eiodiesel. It is heated at about 50° C. until obtaining a solution. Then to the so prepared solution Voranate™ 220 (27.3 g) containing MDI 40% by weight and PAPI 60% by weight is added, the average functionality of the isocyanic monomer mixture is 2.7. It is left then under stirring up to complete dissolution.

Separately, in a 2000 ml glass container an aqueous solution is prepared by mixing 433.7 g of water, 11 g of Reax™ 100 M surfactant; it is left under stirring until complete dissolution and it is heated to 45° C.

The aqueous solution of Reax™ 100 M is put under stirring at 10,000 rpm by means of a Turrax disperser, by quickly adding the previously prepared solution in organic solvent. It is kept under stirring for 3 minutes and then 26.2 g of diaminohexane 40% titre (% w/w) are added and stirring is continued for 15 seconds while reducing the speed to about 6,400 rpm.

The obtained suspension/dispersion of microcapsules is transferred into a 2000 ml reactor for the maturation step (4 hours), under stirring and keeping the suspension at a temperature of 50° C. At the end the suspension of microcapsules is cooled in the reactor at the temperature of 20-25° C. and the product is discharged in a 2000 ml container, wherein the following components are added in the indicated amounts:

| Component | Typology | Grams |
|---|---|---|
| Kobate ™ C | Biocide | 2 |
| Rhodopol ™ 23 Pregel 2.7% | Thickener | 40 |
| Defomex ™ 1510 | Antifoam agent | 2 |
| Propylene glicol | Antifreeze agent | 50 |

The suspension is left under stirring until obtaining an homogeneous suspension.

The composition of the formulation is reported in Table 1.

The average granulometry of the microcapsules, determined by the above reported test, is 3.2 µm.

Example 2

Preparation of the Microcapsule Formulation CS2

The organic solution of Deltamethrin and piperonylbutoxide in biodiesel is prepared as in example 1 (comparative). To this solution 15.5 g of Voranate™ M 220 and 15.5 g of TDI (80% by weight by the isomer 2,4 substituted and 20% by the isomer 2,6 substituted) are added and the mixture is left under stirring up to a complete solubilization.

The Reax™ 100 M solution is prepared by dissolving 11 g of the compound in 456 g of water and stirring until obtaining a limpid solution and it is heated to 45° C.

The successive step is carried out by pouring into the Reax™ 100 M aqueous solution the previously prepared organic solution and maintaining the stirring at 10,000 rpm by a Turrax disperser for a time of 3 minutes.

The maturation step of the microcapsules and the following addition step of the other components of the formulation is carried out as described in Ex. 1 comp.

The composition of the formulation is reported in Table 1.

The average granulometry of the microcapsules is 3 µm.

Example 3

Preparation of the Microcapsule Formulation CS3

The organic solution of Deltamethrin and piperonylbutoxide in Biodiesel is prepared as in example 1 (comparative).

To this solution 23.3 g of Voranate™ M 220 and 0.78 g of TDI of example 2 are added and it is left under stirring up to a complete solubilization of the components.

The Reax™ 100 M solution is prepared by dissolving 11 g of the compound in 455,9 g of water, under stirring until obtaining a limpid solution and it is heated to 45° C.

The addition of the organic solution to the Reax™ 100 M aqueous solution is carried out as described in example 2.

The maturation step of the microcapsules and the addition of the other components of the formulation is carried out as described in Ex. 1 comp.

The composition of the formulation is reported in Table 1.

The average granulometry of the microcapsules is 3.3 µm.

Example 4

Preparation of the Microcapsule Formulation CS4

The organic solution of Deltamethrin and piperonylbutoxide in Biodiesel is prepared as in example 1 (comparative).

To this solution 31 g of Voranate™ M 220 are added and it is left under stirring up to a complete solubilization.

The Reax™ 100 M solution is prepared by dissolving 11 g of the compound in 456 g of water, under stirring until obtaining a limpid solution and heating to 45° C.

The step of addition of the organic solution to the Reax™ 100 M aqueous solution is carried out as described in example 2.

The maturation step of the microcapsules and the addition of the other components of the formulation is carried out as described in Ex. 1 comp.

The composition of the formulation is reported in Table 1.

The average granulometry of the microcapsules is 3.1 µm.

Example 5

Preparation of the Microcapsule Formulation CS5

The organic solution of Deltamethrin and piperonylbutoxide in Biodiesel is prepared as in example 1 (comparative).

To this solution 31 g of Voranate™ M 220 are added and the mixture is left under stirring up to a complete solubilization.

The Reax™ 100 M solution is prepared apart by dissolving 11 g of the compound in 456 g of water, by stirring until obtaining a limpid solution and it is heated to 45° C.

The successive step is carried out by pouring into the Reax™ 100 M aqueous solution the previously prepared organic solution of the active principle and stirring is maintained at 7,600 rpm by a Turrax disperser for a time of 1 minute.

The maturation step of the microcapsules and the addition of the other components of the formulation is carried out as described in Ex. 1 comp.

The composition of the formulation is reported in Table 2.

The average granulometry of the microcapsules is 6.5 µm.

Example 6

Preparation of the Microcapsule Formulation CS6

The organic solution of Deltamethrin and piperonylbutoxide in Biodiesel is prepared as in example 1 (comparative).

To this solution 31 g of Voranate™ M 220 are added and the mixture is left under stirring up to a complete solubilization.

The Reax™ 100 M solution is apart prepared by dissolving 11 g of the compound in 456 g of water, by stirring until obtaining a limpid solution and it is heated to 45° C.

The successive step is carried out by pouring into the Reax™ 100 M aqueous solution the previously prepared organic solution and stirring is maintained at 5200 rpm by a Turrax disperser for a time of 1 minute.

The maturation step of the microcapsules and the addition step of the other components of the formulation is carried out as described in Ex. 1 comp.

The composition of the formulation is reported in Table 2.

The average granulometry of the microcapsules is 12 µm.

Example 7

Preparation of the Microcapsule Formulation CS7

In a 1000 ml glass container a solution of 31 g of Deltamethrin 99%, 0.05 g of piperonyl butoxide in 358 g of Biodiesel is prepared. It is heated up to about 50° C. until a solution is obtained. Then to the so prepared solution 31 g of Voranate™ M 220 are added and the mixture is left under stirring up to a complete solubilization.

The Reax™ 100 M solution is prepared by dissolving 11 g of the compound in 451 g of water, by stirring until obtaining a limpid solution and it is heated to 45° C.

The successive step is carried out by pouring into the Reax™ 100 M aqueous solution the previously prepared organic solution and stirring is maintained at 10,000 rpm by a Turrax disperser for a time of 2 minutes.

The maturation step of the microcapsules and the following addition step of the other components of the formulation is carried out as described in Ex. 1 comp.

The composition of the formulation is reported in Table 2.

The average granulometry of the microcapsules is 3.2 µm.

Example 8

Preparation of the Microcapsule Formulation CS8

The organic solution of Deltamethrin and piperonylbutoxide in Biodiesel is prepared as in example 1 (comparative).

To this solution 16 g of Isonate® 125 M (diphenylmethylen-4,4'-diisocyanate with 98% titre) are added and the mixture is left under stirring up to a complete solubilization.

The Reax™ 100 M solution is prepared by dissolving 11 g of the compound in 471 g of water, by stirring until obtaining a limpid solution and it is heated to 45° C.

The successive step is carried out by pouring into the Reax™ 100 M aqueous solution the previously prepared organic solution and stirring is maintained at 10,000 rpm by a Turrax disperser for a time of 2 minutes.

The maturation step of the microcapsules and the following addition step of the other components of the formulation is carried out as described in Ex. 1 comp.

The composition of the formulation is reported in Table 2.
The average granulometry of the microcapsules is 3.2 μm.

Example 9

Preparation of the Microcapsule Formulation CS9

The organic solution of Deltamethrin and piperonylbutoxide in Biodiesel is prepared as in example 1 (comparative).

To this solution 8 g of Isonate® 125 M (diphenylmethylen-4,4'-diisocyanate 98%) are added and the mixture is left under stirring up to a complete solubilization.

The Reax™ 100 M solution is prepared by dissolving 11 g of the compound in 479 g of water, by stirring until obtaining a limpid solution and it is heated to 45° C.

The successive step is carried out by pouring into the Reax™ 100 M aqueous solution the previously prepared organic solution and stirring is maintained at 10,000 rpm by a Turrax disperser for a time of 2 minutes.

The maturation step of the microcapsules and the successive addition step of the other components of the formulation is carried out as described in Ex. 1 comp.

The composition of the formulation is reported in Table 3.
The average granulometry of the microcapsules is 3.3 μm.

Example 10

Preparation of the Microcapsule Formulation CS11

In a 1000 ml glass container a solution in organic solvent is prepared by weighing 103 g of Lambda Cyhalothrin 97%, 5 g of g of piperonyl butoxide at 94% and 90 g of Solvesso® 200 ND. It is heated to about 50° C. until obtaining a solution. Then to the so prepared solution Voranate™ M 220 (16 g) containing 40% by weight of MDI and the remaining part PAPI, is added, the average functionality of the mixture is 2.7. It is left then under stirring up to complete dissolution.

Separately, in a 2000 ml glass container an aqueous solution is prepared by adding 500 g of water, 11 g of the Reax™ 100 N surfactant and leaving under stirring until complete dissolution and it is heated to 45° C.

The aqueous solution of Reax™ 100 M is put under stirring at 7600 rpm by means of a type Turrax disperser, by quickly adding the previously prepared solution in organic solvent containing the active principle. It is kept under stirring for 1 minute.

The obtained suspension/dispersion of microcapsules is transferred into a 2000 ml reactor for the maturation step (4 hours), under stirring and maintaining in the suspension a temperature of 50° C. At the end the suspension of microcapsules is cooled in the reactor at the temperature of 20-25° C. and the product is discharged in a 2000 ml container, wherein the following components are added in the indicated amounts:

| Component | Typology | Grams |
|---|---|---|
| Kobate ™ C | Biocide | 1 |
| Rhodopol ™ 23 Pregel 2.7% | Thickener | 70 |
| Defomex ™ 1510 | Antifoam agent | 2 |
| Propylene Glycol | Antifreeze agent | 5 |
| Water | Completion | 152 |

Once the addition of the above components is ended, the suspension is left under stirring until obtaining an homogeneous suspension.

The composition of the formulation is reported in Table 3.
The average granulometry of the microcapsules is 8.9 μm.

Example 11

Preparation of the Microcapsule Formulation CS12

The organic solution of Lambda Cyhalothrin and piperonylbutoxide in Solvesso® 200 ND is prepared as in example 11.

To this solution 8 g of Voranate® M 220 and 8 g of TDI (80% by weight of isomer 2,4 substituted and 20% of isomer 2,6 substituted) are added and the mixture is left under stirring up to a complete solubilization.

The Reax™ 100 M solution is prepared by dissolving 11 g of the compound in 500 g of water, and stirring until obtaining a limpid solution and it is heated to 45° C.

The successive step is carried out by pouring into the Reax™ 100 M aqueous solution the previously prepared organic solution and stirring is maintained at 7600 rpm by a Turrax disperser for a time of 1 minute.

The maturation step of the microcapsules and the addition step of the other components of the formulation is carried out as described in Ex. 11.

The composition of the formulation is reported in Table 3.
The average granulometry of the microcapsules is 8.3 μm.

Example 12

Preparation of the Microcapsule Formulation CS13

The organic solution of Lambda Cyhalothrin and piperonylbutoxide in Solvesso® 200 ND is prepared as in example 11.

To this solution 8 g of Voranate® M 220 and 8 g of Isonate® 125 M (diphenylmethylen-4,4'diisocyanate 98%) are added and the mixture is left under stirring up to a complete solubilization.

The Reax™ 100 M solution is prepared by dissolving 11 g of the compound in 500 g of water and stirring until obtaining a limpid solution and it is heated to 45° C.

The successive step is carried out by pouring in the Reax™ 100 M aqueous solution the previously prepared organic solution and stirring is maintained at 7600 rpm by a Turrax disperser for a time of 1 minute.

The maturation step of the microcapsules and the successive addition step of the other components of the formulation is carried out as described in Ex. 11.

The composition of the formulation is reported in Table 4.
The average granulometry of the microcapsules is 7.9 μm.

Example 13

Preparation of the Microcapsule Formulation CS14

The organic solution of Lambda Cyhalothrin and piperonylbutoxide in Solvesso® 200 ND is prepared as in example 11.

To this solution 6.5 g of TDI 80 (80% by weight of isomer 2,4 substituted and 20% of isomer 2,6 substituted) and 9.5 g of Isonate® 125 M (diphenylmethylen-4,4'diisocyanate 98%) are added and the mixture is left under stirring up to a complete solubilization.

The Reax™ 100 M solution is prepared by dissolving 11 g of the compound in 500 g of water, by stirring until obtaining a limpid solution and it is heated to 45° C.

The successive step is carried out by pouring into the Reax™ 100 M aqueous solution the previously prepared organic solution and stirring is maintained at 7600 rpm by a Turrax disperser for a time of 1 minute.

The maturation step of the microcapsules and the successive addition step of the other components of the formulation is carried out as described in E. 11.

The composition of the formulation is reported in Table 4.

The average granulometry of the microcapsules is 8.6 μm.

TABLE 1

The amounts reported in the Table are % by weight

| Example<br>Formulation | 1 comp<br>CS1 | 2<br>CS2 | 3<br>CS3 | 4<br>CS4 |
|---|---|---|---|---|
| Deltamethrin 99% | 3.10 | 3.10 | 3.10 | 3.10 |
| Piperonyl Butoxide 95% | 15.80 | 15.80 | 15.80 | 15.80 |
| Biodiesel | 20.00 | 20.00 | 20.00 | 20.00 |
| Voranate ™ M 220 | 2.73 | 1.55 | 2.33 | 3.10 |
| 1,6 Diaminohexane 40% | 2.60 | — | — | — |
| TDI | — | 1.55 | 0.78 | — |
| Reax ™ 100 M | 1.10 | 1.10 | 1.10 | 1.10 |
| Propilene glycol | 5.00 | 5.00 | 5.00 | 5.00 |
| Defomex ™ 1510 | 0.20 | 0.20 | 0.20 | 0.20 |
| Kobate ™ C | 0.10 | 0.10 | 0.10 | 0.10 |
| Rhodopol ™ 23 pregel. 2.7% | 6.00 | 6.00 | 6.00 | 6.00 |
| Water | 43.37 | 45.60 | 45.59 | 45.60 |

TABLE 2

The reported amounts in the Table are % by weight

| Example<br>Formulation | 5<br>CS5 | 6<br>CS6 | 7<br>CS7 | 8<br>CS8 |
|---|---|---|---|---|
| Deltamethrin 99% | 3.1 | 3.1 | 3.1 | 3.1 |
| Piperonyl Butoxide 95% | 15.8 | 15.8 | 0.5 | 15.8 |
| Biodiesel | 20.0 | 20.0 | 35.8 | 20.0 |
| Voranate ™ M 220 | 3.1 | 3.1 | 3.1 | — |
| Isonate ® 125 M | — | — | — | 1.6 |
| Reax ™ 100 M | 1.1 | 1.1 | 1.1 | 1.1 |
| Propylene Glycol | 5.0 | 5.0 | 5.0 | 5.0 |
| Defomex ™ 1510 | 0.2 | 0.2 | 0.2 | 0.2 |
| Kobate ™ C | 0.1 | 0.1 | 0.1 | 0.1 |
| Rhodopol ™ 23 pregel. 2.7% | 6.0 | 6.0 | 6.0 | 6.0 |
| Water | 45.6 | 45.6 | 45.1 | 47.1 |

TABLE 3

The amounts reported in the Table are % by weight

| Example<br>Formulation | 9<br>CS9 | 10<br>CS11 | 11<br>CS12 |
|---|---|---|---|
| Deltamethrin 99% | 3.1 | — | — |
| Lambda Cyhalothrin 97% | — | 10.3 | 10.3 |
| Solvesso ® 200 ND | — | 9.0 | 9.0 |
| Piperonyl Butoxide 95% | 15.8 | 0.5 | 0.5 |
| Biodiesel | 20.0 | — | — |
| Voranate ™ M 220 | — | 1.6 | 0.8 |
| TDI 80 | — | — | 0.8 |
| Isonate ® 125 M | 0.8 | — | — |
| Reax ™ 100 M | 1.1 | 1.1 | 1.1 |
| Propylene Glycol | 5.0 | 5.0 | 5.0 |
| Defomex ™ 1510 | 0.2 | 0.2 | 0.2 |
| Kobate ™ C | 0.1 | 0.1 | 0.1 |
| Rhodopol ™ 23 pregel. 2.7% | 6.0 | 7.0 | 7.0 |
| Water | 47.9 | 65.2 | 65.2 |

TABLE 4

The amounts reported in the Table are % by weight

| Example<br>Formulation | 12<br>CS13 | 13<br>CS14 |
|---|---|---|
| Lambda cyhalothrin 97% | 10.3 | 10.3 |
| Piperonyl Butoxide 95% | 0.5 | 0.5 |
| Solvesso ® 200 ND | 9.0 | 9.0 |
| Voranate ™ M 220 | 0.8 | — |
| TDI 80 | — | 0.65 |
| Isonate ® 125 M | 0.8 | 0.95 |
| Reax ™ 100 M | 1.1 | 1.1 |
| Propylene Glycol | 5.0 | 5.0 |
| Defomex ™ 1510 | 0.2 | 0.2 |
| Kobate ™ C | 0.1 | 0.1 |
| Rhodopol ™ 23 pregel. 2.7% | 7.0 | 7.0 |
| Water | 65.2 | 65.2 |

Example 14

Evaluation of the Knockdown and Killing Effect of the Formulations of Examples 1-4

The test is carried out according to the above mentioned modalities. The comparison has been made with the emulsifiable concentrates (EC) containing deltamthrin (DTM) indicated above and with the product Demand CS™ containing lambda cyhalothrin to evaluate the knockdown and killing effects prolonged in the time, as indicated above.

The results are reported in Table 5.

TABLE 5

Knockdown (kd) and mortality (m) values expressed in % of treated insects- t = time

| Used formulation | t = 0 | | T 7 days | | t 1 month | | t 3 months | | t 6 months | | t 9 months | |
|---|---|---|---|---|---|---|---|---|---|---|---|---|
| | 1 h Kd | 24 h m | 1 h Kd | 24 h M | 1 h Kd | 24 h m | 1 h Kd | 24 h m | 1 h Kd | 24 h m | 1 h Kd | 24 h m |
| Example 1 | 100 | 100 | 37 | 100 | 7 | 83 | 43 | 60 | 67 | 67 | 0 | 30 |
| Example 2 | 100 | 100 | 100 | 100 | 85 | 100 | 55 | 93 | 100 | 100 | 67 | 100 |
| Example 3 | 96 | 100 | 100 | 100 | 81 | 100 | 37 | 67 | 100 | 100 | 77 | 100 |
| Example 4 | 100 | 100 | 100 | 100 | 89 | 100 | 87 | 100 | 100 | 100 | 81 | 100 |
| DTM + PBO EC | 100 | 100 | 0 | 17 | 3 | 16 | 0 | 3 | 0 | 0 | 0 | 0 |

TABLE 5-continued

| | Knockdown (kd) and mortality (m) values expressed in % of treated insects- t = time | | | | | | | | | | | |
|---|---|---|---|---|---|---|---|---|---|---|---|---|
| | t = 0 | | T 7 days | | t 1 month | | t 3 months | | t 6 months | | t 9 months | |
| Used formulation | 1 h Kd | 24 h m | 1 h Kd | 24 h M | 1 h Kd | 24 h m | 1 h Kd | 24 h m | 1 h Kd | 24 h m | 1 h Kd | 24 h m |
| DTM EC | 23 | 30 | 0 | 10 | 3 | 13 | 0 | 10 | 0 | 0 | 0 | 0 |
| DEMAND ® CS | 94 | 100 | 100 | 100 | 69 | 100 | 58 | 100 | 70 | 90 | 0 | 100 |
| Untreated controls | 0 | 0 | 13 | 13 | 3 | 13 | 0 | 0 | 0 | 0 | 0 | 0 |

Example 15

Preparation of the Formulation of Microcapsules CS15

Example 10 is repeated but using 16 g of Isonate® 125 M instead of Voranate™ M 220.

The composition of the formulation is reported in Table 6.

Example 16

Preparation of the Formulation of Microcapsules CS16

In a 1000 ml glass reactor a mixture formed of 26 g of Imidachloprid 96% purity, 5 g of piperonyl butoxide 94% purity and 400 g of Purasolv®EHL (etylhexyl lactate) is prepared. It is heated at about 50° C. until obtaining an homogeneous solution. Then to the so prepared solution Voranate™ M 220 (43.48 g) containing MDI 40% by weight and PAPI 60% by weight is added, the average functionality of the isocyanic monomer mixture is 2.7. It is left then under stirring up to complete dissolution.

Separately, in a 2000 ml glass container an aqueous solution is prepared by mixing 330 g of water, 11 g of Reax™ 100 M surfactant; it is left under stirring until complete dissolution and it is heated to 45° C.

The step of admixing the aqueous solution of Reax™ 100 M with the previously prepared organic solution containing the active ingredient and the subsequent microcapsule suspension/dispersion maturation step are carried out as described in example 10.

At the end the suspension of microcapsules is cooled in the reactor at a temperature of 20-25° C. and the product is discharged in a 2000 ml container, wherein the following components are added in the indicated amounts:

| Component | Typology | Grams |
|---|---|---|
| Kobate ™ C | Biocide | 1 |
| Rhodopol ™ 23 Pregel 2.7% | Thickener | 40 |
| Defomex ™ 1510 | Antifoam agent | 2 |
| Propylene glicol | Antifreeze agent | 50 |
| water | | 100.52 |

The suspension is left under stirring until obtaining an homogeneous suspension.

The composition of the formulation is reported in Table 6.

The average granulometry of the microcapsules is 8.6 μm.

Example 17

Preparation of the Formulation of Microcapsules CS17

In a 1000 ml glass reactor a mixture formed of 26 g of Imidachloprid 96% purity, 25.2 g of Deltamethrin 99% purity, 5 g of piperonyl butoxide 94% purity and 400 g of Purasolv®EHL (etylhexyl lactate) is prepared. It is heated at about 50° C. until obtaining an homogeneous solution. Then to the so prepared solution Voranate™ M 220 (36.5 g) containing MDI 40% by weight and PAPI 60% by weight is added, the average functionality of the isocyanic monomer mixture is 2.7. It is left then under stirring up to complete dissolution.

Separately, in a 2000 ml glass container an aqueous solution is prepared by mixing 313.3 g of water, 11 g of Reax™ 100 M surfactant; it is left under stirring until complete dissolution and it is heated to 45° C.

The steps of admixing the aqueous solution of Reax™ 100 M with the previously prepared organic solution containing the active ingredients, and the subsequent microcapsule suspension/dispersion maturation are carried out as described in example 10.

At the end the suspension of microcapsules is cooled in the reactor at a temperature of 20-25° C. and the product is discharged in a 2000 ml container, wherein the following components are added in the indicated amounts:

| Component | Typology | Grams |
|---|---|---|
| Kobate ™ C | Biocide | 1 |
| Rhodopol ™ 23 Pregel 2.7% | Thickener | 30 |
| Defomex ™ 1510 | Antifoam agent | 2 |
| Propylene glicol | Antifreeze agent | 50 |
| water | | 100.3 |

The suspension is left under stirring until obtaining an homogeneous suspension.

The composition of the formulation is reported in Table 6.

The average granulometry of the microcapsules is 8.8 μm.

TABLE 5

| Example Formulation | 15* CS15 | 16* CS16 | 17* CS17 |
|---|---|---|---|
| Imidachloprid 96% | — | 2.6 | 2.6 |
| Deltamethrin 99% | — | — | 2.52 |
| Lambda Cyhalothrin 97% | 10.3 | — | — |
| Piperonyl Butoxide 95% | 0.5 | 0.5 | 0.5 |
| Solvesso ® 200 ND | 9.0 | — | — |

TABLE 5-continued

| Example<br>Formulation | 15*<br>CS15 | 16*<br>CS16 | 17*<br>CS17 |
|---|---|---|---|
| Purasolv ®EHL | — | 40.0 | 40.0 |
| Voranate ™ M 220 | — | 3.45 | 3.65 |
| Isonate ® 125 M | 1.6 | — | — |
| Reax ™ 100 M | 1.1 | 1.1 | 1.1 |
| Propilene Glycol | 5.0 | 5.0 | 5.0 |
| Defomex ™ 1510 | 0.2 | 0.2 | 0.2 |
| Kobate ™ C | 0.1 | 0.1 | 0.1 |
| Rhodopol ™ 23 pregel. 2.7% | 7.0 | 4.0 | 3.0 |
| Water | 65.2 | 43.05 | 41.33 |

*Amounts reported are in % by weight

The invention claimed is:

1. A method of fighting insects comprising contacting the insects with formulations having a prolonged knockdown and insecticidal activity at least longer than three months from the contacting, said formulations comprising microcapsules with polyurea walls obtainable by interfacial polymerization of diphenylmethylen-4,4'-diisocyanate (MDI), wherein the microcapsules comprise:
an active principle selected from the pyrethroid and/or neonicotinoid classes, synergizing agents selected from piperonylbutoxide (PBO) and 4-[1-(2-butin-1 -yloxy) ethyl]-1,2- di-methoxy benzene (Verbutin),
the concentration of the active principle in the microcapsule as % by weight on the total of the micro-capsule ranges from 1 % to 60 %, the average diameter of the microcapsule ranges from 2 to 50 μm.

2. The method according to claim 1 wherein the polyurea of the microcapsule walls is obtainable by interfacial polymerization of diphenylmethylen-4,4'-diisocyanate (MDI) in the presence of polymethylenepolyphenylisocyanate (PAPI).

3. The method according to claim 1 wherein the polyurea of the microcapsule walls is obtainable by using an amount by weight of MDI with respect to PAPI comprised between 20:80 and 80:20.

4. The method according to claim 1 wherein the weight ratio synergizing agent/active principle is comprised between 0.02 and 50.

5. The method according to claim 1 wherein the polyurea of the microcapsule walls is obtainable by using TDI in combination with MDI, the ratio by weight between MDI and TDI being comprised between 10:90 and 100:0.

6. The method according to claim 5 wherein TDI is used in combination with MDI and PAPI.

7. The method according to claim 1 wherein the microcapsules comprise organic solvents having:
low volatility,
solubilization of the active principle at room temperature at least at a concentration of 1 % by weight, substantial immiscibility with water.

8. The method according to claim 7, wherein the organic solvents are selected from:
$C_9$-$C_{20}$ alkyklbenzenes, and their mixture, wherein the alkyl is linear or branched, $C_1$-$C_4$ alkyl esters of $C_3$-$C_{14}$ bicarboxylic acids, $C_9$-$C_{10}$ alkyl esters of carboxylic acids or $C_3$-$C_{10}$ aliphatic hydroacids or their mixtures, and methyl esters of saturated or unsaturated $C_{12}$-$C_{22}$ fatty acids or their mixture, $C_7$-$C_9$ alkyl esters of the acetic acid.

9. The method according to claim 1 wherein pyrethroids are selected from: d-Allethrin, Bifenthrin, Cyfluthrin, β-Cyfluthrin, λ-Cyhalothrin,. Cypermethrin, α-Cypermethrin, Deltamethrin, Esbiothrin, Etofenprox, Phenothrin, d-Phenothrin, lmiprothrin, Metofluthrin, Permethrin, Prallethrin, Tetramethrin, d-Tetramethrin, Trans-fluthrin, pyrethrum extracts and their mixtures.

10. The method according to claim 1 wherein neonicotinoids are selected from: Acetamiprid, Imidachloprid, and Thiachloprid.

11. The method according to claim 1 wherein the formulations of pyrethroids and neonicotinoids are used for professional applications, for domestic applications for the disinfestation of stables and sheds of domestic animals and of residential and industrial areas.

12. Formulations of microcapsules having polyurea walls obtainable by interfacial polymerization of the isocyanic monomer diphenylmethylen-4,4"-diisocyanate (MDI), wherein the microcapsules comprise:
an active principle selected from pyrethroid and neonicotinoid classes,
synergizing agents selected from piperonylbutoxide (PBO) and Verbutin,
the concentration of the active principle in the microcapsule as % by weight on the total one of the microcapsule ranges from 1 % to 60%,
the capsule average diameter ranging from 2 to 50 μm.

13. Formulations of microcapsules according to claim 12 wherein the polyurea wall of the microcapsule is obtainable by interfacial polymerization of MDI in the presence of PAPI.

14. Formulations according to claim 12 wherein the polyurea wall of the microcapsule is obtainable by interfacial polymerization of TDI in combination with MDI.

15. Formulations according to claim 12 wherein the polyurea wall of the microcapsule is obtainable by interfacial polymerization of TDI in combination with MDI and PAPI.

16. Formulations of microcapsules according to claim 12 wherein the synergizing agent is PBO.

17. Formulations of microcapsules according to claim 12 comprising one or more of dispersing agents, thickeners, antifoam, antifreeze, antimould agents, photoprotectors and adhesivants.

18. Formulations of microcapsules according to claim 12 wherein the photoprotecting agents are selected from benzotriazoles, benzophenones and sterically hindered amines (HALS).

19. A process for preparing microcapsules of the formulations of claim 12 comprising the following steps:
(1) preparation of an aqueous phase containing at least a surfactant,
(2) preparation of an oil phase containing an active principle selected from the pyrethroid and/or neonicotinoid classes, a synergizing agent selected between PBO and Verbutin and the isocyanic monomeric reactant methylenphenylen-4,4'-diisocyanate (MDI),
the oil phase (2) is added to the aqueous phase (1) for obtaining the polyurea microcapsule.

20. A process according to claims 19 wherein in step (2) MDI is used in combination with PAPI.

21. A process according to claim 19 wherein in step (2) TDI is used in combination with MDI.

22. A process according to claim 19 wherein in step (2) TDI is used in combination with MDI and PAPI.

23. A process according to claim 19, wherein in step (2) organic solvents are added.

24. The method of claim 1 wherein said formulations are adapted to provide a prolonged knockdown and insecticidal activity even longer than 6 months from the application.

25. The method of claim 1 wherein said formulations are adapted to provide a prolonged knockdown and insecticidal activity even longer than 9 months from the application.

26. Formulations of microcapsules according to claim 12, wherein the concentration of the active principle in the microcapsule as % by weight on the total one of the microcapsule ranges from 2.5 % to 55%.

27. Formulations of microcapsules according to claim 12, wherein the concentration of the active principle in the microcapsule as % by weight on the total one of the microcapsule ranges from 5 % to 50%.

28. Formulations of microcapsules according to claim 12, wherein the capsule average diameter ranges from 5 to 30 μm.

29. Formulations of microcapsules according to claim 12, wherein the capsule average diameter ranges from 6 to 20 μm.

* * * * *